US008476014B2

(12) United States Patent  
Yeh et al.

(10) Patent No.: US 8,476,014 B2
(45) Date of Patent: Jul. 2, 2013

(54) PROBE AND METHOD FOR DNA DETECTION

(75) Inventors: Hsin-Chih Yeh, Los Alamos, NM (US); James Henry Werner, Los Alamos, NM (US); Jaswinder Kumar Sharma, Los Alamos, NM (US); Jennifer Suzanne Martinez, Dixon, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 229 days.

(21) Appl. No.: 12/932,321

(22) Filed: Feb. 22, 2011

(65) Prior Publication Data

US 2011/0212540 A1 Sep. 1, 2011

Related U.S. Application Data

(60) Provisional application No. 61/338,461, filed on Feb. 19, 2010.

(51) Int. Cl.
*C12Q 1/68* (2006.01)
*C12N 15/11* (2006.01)

(52) U.S. Cl.
USPC .................... 435/6.1; 536/23.1; 536/24.3

(58) Field of Classification Search
None
See application file for complete search history.

(56) References Cited

U.S. PATENT DOCUMENTS

| 7,611,907 B2 | 11/2009 | Dickson et al. |
| 7,867,726 B2 | 1/2011 | Wood et al. |
| 7,871,799 B2 | 1/2011 | Gardner et al. |

FOREIGN PATENT DOCUMENTS

| JP | 2006-316237 | 11/2006 |
| WO | 2005/086830 | 9/2005 |
| WO | 2006/050257 | 5/2006 |
| WO | 2007/120762 | 10/2007 |

OTHER PUBLICATIONS

Gwinn et al, Advanced Materials 20 (2), 279 (2008).*
Affleck et al., "Reduction of Luminescent Background in Ultrasensitive Fluorescence Detection by Photobleaching," Analytical Chemistry 68(13):2270-2276, Jul. 1, 1996.
Antoku, "Fluorescent Polycytosine-Encapsulated Silver Nanoclusters," Georgia Institute of Technology, May 2007.
Babendure et al., "Aptamers Switch on Fluorescence of Triphenylmethane Dyes," J. Am. Chem. Soc. 125 (48):14716-14717, Nov. 8, 2003.
Bonnet et al., "Kinetics of conformational fluctuations in DNA hairpin-loops," Proc. Natl. Acad. Sci. USA 95 (15):8602-8606, Jul. 1998.
Bonnet et al., "Thermodynamic basis of the enhanced specificity of structured DNA probes," Proc. Natl. Acad. Sci. USA 96(11):6171-6176, May 1999.
Bratu et al., "Visualizing the distribution and transport of mRNAs in living cells," Proc. Natl. Acad. Sci. USA 100(23):13308-13313, Nov. 11, 2003.
Cabantous et al., "Protein tagging and detection with engineered self-assembling fragments of green fluorescent protein," Nature Biotechnology 23(1):102-107, Dec. 5, 2004.
Chen et al., "Highly sensitive biological and chemical sensors based on reversible fluorescence quenching in a conjugated polymer," Proc. Natl. Acad. Sci. USA 96(22):12287-12292, Oct. 26, 1999.
Fang et al., "Designing a Novel Molecular Beacon for Surface-Immobilized DNA Hybridization Studies," J. Am. Chem. Soc. 121(12):2921-2922, Mar. 11, 1999.
Griffin et al., "Specific Covalent Labeling of Recombinant Protein Molecules Inside Living Cells," Science 281 (5374):269-272, Jul. 10, 1998.
Guo et al., "Oligonucleotide-stabilized Ag nanoclusters as novel fluorescence probes for the highly selective and sensitive detection of the Hg2+ ion," Chem Commun. (23):3395-3397, Apr. 27, 2009.
Guo et al., "Highly Sequence-Dependent Formation of Fluorescent Silver Nanoclusters in Hybridized DNA Duplexes for Single Nucleotide Mutation Identification," J. Am. Chem. Soc. 132(3):932-934, Dec. 28, 2009.
Heinlein et al., "Photoinduced Electron Transfer between Fluorescent Dyes and Guanosine Residues in DNA-Hairpins," J. Phys. Chem. 107(31):7957-7964, Jul. 4, 2003.
Knemeyer et al., "Probes for Detection of Specific DNA Sequences at the Single-Molecule Level," Anal Chem. 72 (16):3717-3724, Jul. 8, 2000.
Lan et al., "Silver nanoclusters as fluorescent probes for selective and sensitive detection of copper ions," Chem Commun. 46(8):1257-1259, Jan. 18, 2010.
Mayer et al., "Robust Nano Cluster Layers for Structural Amplified Fluorescence Biochips," Rev. Adv. Mater. Sci. 5 (1):53-56, 2003.
Miyawaki et al., "Fluorescent indicators for Ca2+ based on green fluorescent proteins and calmodulin," Nature 388 (6645):882-887, Aug. 1997.
Nazarenko et al., "Effect of primary and secondary structure of oligodeoxyribonucleotides on the fluorescent properties of conjugated dyes," Nucleic Acids Research 30(9):2089-2195, 2002.
Nolan et al., "A Simple Quenching Method for Fluorescence Background Reduction and Its Application to the Direct, Quantitative Detection of Specific mRNA," Anal Chem. 75:6236-6243, Sep. 30, 2003.
Patel et al., "Water-Soluble Ag Nanoclusters Exhibit Strong Two-Photon-Induced Fluorescence," J. Am. Chem. Soc. 130(35):11602-11603, 2008.
Patel et al., "Electron Transfer-Induced Blinking in Ag Nanodot Fluorescence," J. Phys. Chem. C 113 (47):20264-20270, Nov. 2, 2009.

(Continued)

*Primary Examiner* — James Martinell
(74) *Attorney, Agent, or Firm* — Samuel L. Borkowsky

(57) ABSTRACT

A hybridization probe containing two linear strands of DNA lights up upon hybridization to a target DNA using silver nanoclusters that have been templated onto one of the DNA strands. Hybridization induces proximity between the nanoclusters on one strand and an overhang on the other strand, which results in enhanced fluorescence emission from the nanoclusters.

12 Claims, 5 Drawing Sheets

OTHER PUBLICATIONS

Petty et al., "DNA-Templated Ag Nanocluster Formulation," J. Am. Chem. Soc. 126(16):5207-5212, Apr. 2, 2004.

Piestert et al., "A Single-Molecule Sensitive DNA Hairpin System Based on Intramolecular Electron Transfer," Nano Letters 3(7):979-982, May 15, 2003.

Raj et al., "Imaging individual mRNA molecules using multiple singly labeled probes," Nature Methods 5(10):877-879, Oct. 2008.

Richards et al., "Oligonucleotide-Stabilized Ag Nanocluster Fluorophores," J. Am. Chem. Soc. 130(15):5038-5039, Mar. 18, 2008.

Ritchie et al., "Ag Nanocluster Formation Using a Cytosine Oligonucleotide Template," J. Phys. Chem. C 111 (1):175-181, Nov. 17, 2006.

Sauer et al., "Dynamics of the electron transfer reaction between an oxazine dye and DNA oligonucleotides monitored on the single-molecule level," Chemical Physical Letters 284(3-4):153-163, Feb. 27, 1998.

Seidel et al., "Nucleobase-Specific Quenching of Fluorescent Dyes. 1. Nucleobase One-Electron Redox Potentials and Their Correlation with Static Dynamic Quenching Efficiencies," J. Phys. Chem. 100(13):5541-5553, Feb. 15, 1996.

Sengupta et al., "Base-Directed Formation of Fluorescent Silver Clusters," J. Phys. Chem. C 112(48):18776-18782, Nov. 11, 2008.

Sharma et al., "A complementary palette of fluorescent silver nanoclusters," Chem. Commun. 46(19):3280-3282, 2010.

Sokol et al., "Real time detection of DNA-RNA hybridization in living cells," Proc. Natl. Acad. Sci. USA 95:11538-11543, Sep. 1998.

Su et al., "Detection of Copper Ions Through Recovery of the Fluorescence of DNA-Templated Copper/Silver Nanoclusters in the Presence of Mercaptopropionic Acid," Anal. Chem. 82(20):8566-8572, Oct. 15, 2010.

Svanvik et al., "Light-Up Probes: Thiazole Orange-Conjugated Peptide Nucleic Acid for Detection of Target Nucleic Acid in Homogeneous Solution," Analytical Biochemistry 281(1):26-35, 2000.

Torimura et al., "Fluorescence-Quenching Phenomenon by Photoinduced Electron Transfer between a Fluorescent Dye and a Nucleotide Base," Analytical Sciences 17(1):155-160, Jan. 2001.

Tyagi et al., "Molecular Beacons: Probes that Fluoresce upon Hybridization," Nature Biotechnology 14(3):303-308, Mar. 1996.

Tyagi et al., "Multicolor molecular beacons for allele discrimination," Nature Biotechnology 16(1):49-53, Jan. 1998.

Vosch et al., "Strongly emissive individual DNA-encapsulated AG nanoclusters as single-molecule fluorophores," Proc. Natl. Acad. Sci. USA 104(31):12616-12621, Jul. 31, 2007.

Widengren et al., "Fast interactions between Rh6G and dGTP in water studied by fluorescence correlation spectroscopy," Chemical Physics 216(3):417-426, 1997.

Yang et al., "Molecular Assembly of Superquenchers in Signaling Molecular Interactions," J. Am. Chem. Soc. 127 (37):12772-12773, Aug. 23, 2005.

Yeh et al., "Tunable Blinking Kinetics of Cy5 for Precise DNA Quantification and Single-Nucleotide Difference Detection," Biophysical Journal 95(2):729-737, Jul. 2008.

Yeh et al., "A DNA-Silver Nanocluster Probe that Fluoresces upon Hybridization," Nano Letters 10(8):3106-3110, Jul. 19, 2010.

Yeh et al., "Photophysical characterization of fluorescent metal nanoclusters synthesized using oligonucleotides, proteins and small molecule ligands," Proc of SPIE 7576, 2010.

Yu et al., "Live Cell Surface Labeling with Fluorescent Ag Nanocluster Conjugates," Photochemistry and Photobiology 84(6):1435-1439, 2008.

Yu et al., "Shuttle-Based Fluorogenic Silver-Cluster Biolabels," Angew. Chem. Int. Ed. 48(2):318-320, Dec. 3, 2008.

* cited by examiner

Strand_1 is SEQ ID NO: 1

Strand_RC_15G is SEQ ID NO: 12

| Sample number | Complement | Sequence |
|---|---|---|
| 1 | None | none |
| 2 | Strand_HC | SEQ ID NO: 4 |
| 3 | Strand_HC_1G | SEQ ID NO: 6 |
| 4 | Strand_HC_3G | SEQ ID NO: 7 |
| 5 | Strand_HC_5G | SEQ ID NO: 8 |
| 6 | Strand_HC_7G | SEQ ID NO: 9 |
| 7 | Strand_1C_7G | SEQ ID NO: 5 |
| 8 | Strand_HC_10G | SEQ ID NO: 10 |
| 9 | Strand_HC_13G | SEQ ID NO: 11 |
| 10 | Strand_HC_15G | SEQ ID NO: 12 |

NC probe = SEQ ID NO: 16

G-rich probe = SEQ ID NO: 17

PROBE AND METHOD FOR DNA DETECTION

RELATED APPLICATIONS

This application claims the benefit of the filing date of U.S. Provisional Patent Application Ser. No. 61/338,461 entitled "Fluorescence-Enhancement of DNA-Silver Nanoclusters from Guanine Proximity," filed Feb. 19, 2010, hereby incorporated by reference.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to a probe for detecting a target DNA by an enhanced fluorescence emission when the probe hybridize with the target DNA, and to a method for detecting the target DNA using the probe.

BACKGROUND OF THE INVENTION

The detection and quantification of specific biomolecules, ions, or metabolites are important for in vivo real-time monitoring of cellular processes and for in vitro biosensing and clinical diagnosis. Of the fluorescent probes used for these applications, those that enable detection without separation from the target are more desirable, especially for intracellular studies where removal of unbound probes is difficult. To this end, a number of detection strategies have been developed using reporters that fluoresce upon probe-target binding, including split green fluorescent proteins, electron transfer-based probes, biarsenic organic dyes intercalating dyes, fluorescence resonance energy transfer (FRET)-based indicators, and molecular beacons.

A molecular beacon ("MB") is hairpin-shaped nucleic acid probe that fluoresces upon hybridization with a specific DNA target. MBs have been used much since their introduction in 1996. While successful as a separation-free probe, a MB is generally limited by background fluorescence that comes from imperfect quenching of donors and conformational fluctuations of the hairpin structure. Well-designed MBs can achieve a signal-to-background ratio (S/B ratio) of more than 100-fold but often require special quenchers or sophisticated thermodynamic analysis for stem-loop sequence selection. Additionally, a MB needs to be labeled with a donor fluorophore and a quencher. Therefore, MBs suffer from problems associated with double labeling (e.g. high cost, low yield, singly labeled impurities, extensive purification etc).

Better probes and methods for detecting a target DNA are desirable.

Noble metal nanoclusters, such as those made of silver, gold, copper or other noble metals are collections of small numbers of metal atoms (2-30 atoms) with physical sizes close to the Fermi wavelength of an electron (~0.5 nm for gold and silver). They behave like molecular systems and yield fluorescence emission in the UV-visible range. For example, it has been known for a few years that certain DNA bases and sequences can act as templates for stabilization of fluorescent silver nanoclusters. The resulting oligonucleotide-templated silver nanoclusters ("DNA/Ag NCs") are a versatile set of fluorophores. They have been used for a variety of applications including live cell imaging, detection of specific metal ions, and single-nucleotide variation identification. These DNA/Ag NCs are very small, relatively simple to prepare, and biocompatible (they are made of Ag). They have much better photostability than commonly used organic dyes and may also be a few times brighter. Unlike organic dyes and photoluminescent nanocrystals, they are subject to silver oxidation/reduction or nanocluster ("NC") regrouping, which results in conversion among different NC species. These different species may have different colors. The conversion amongst different NC species is not well understood, but may be reversible and depends on a number of factors including time, temperature, oxygen and salt content.

An object of the invention is to provide a probe for detecting a target DNA by fluorescence emission upon hybridization with the target DNA.

Another object of the invention is to provide a method for detecting a target DNA using a probe that produces an enhanced fluorescence emission upon hybridizing with the target DNA.

SUMMARY OF THE INVENTION

To achieve the foregoing and other objects, and in accordance with the purposes of the present invention, as embodied and broadly described herein, the present invention provides a probe for detecting a target DNA. The DNA target has nucleotide sequence. The probe includes a first strand and a second strand. The first strand includes
  (i) a nucleotide sequence that complements, and can hybridize with, a first portion of the nucleotide sequence of the DNA target,
  (ii) an end portion that does not hybridize with the DNA target and comprises templated fluorescent metal nanoclusters.

The second strand includes
  (iii) a nucleotide sequence that complements, and can hybridize with, the second nucleotide sequence of the DNA target, and
  (iv) an end portion that does not hybridize with the DNA target and would enhance the fluorescence emission from the nanoclusters if it were in sufficient proximity to the nanoclusters.

In a preferred embodiment, the first portion of the nucleotide sequence of the DNA target is adjacent the second portion of the nucleotide sequence of the DNA target. Upon hybridizing the first and second strands of the probe to the DNA target, the proximity of the end portion to the nanoclusters results in enhancement of fluorescence emission from the nanoclusters. In another preferred embodiment, the first portion of the nucleotide sequence of the DNA target is adjacent the second portion of the nucleotide sequence of the DNA target, and the first and second strand hybridize with the DNA target and also partially with each other to produce a stem.

The invention also includes a method for detecting a DNA target. The method includes providing a DNA target comprising a nucleotide sequence and providing a fluorescent probe for detecting the DNA target. The probe includes a first strand and a second strand. The first strand has
  (i) a nucleotide sequence portion that complements, and can hybridize with, a first portion of the nucleotide sequence of the DNA target,
  (ii) an end portion that does not hybridize with the DNA target and is selected for its ability to enhance the fluorescence emission of the nanoclusters if it were in sufficient proximity to the nanoclusters, the second strand having
  (iii) a nucleotide sequence portion that complements, and can hybridize with, a second portion of the nucleotide sequence of the DNA target, and
  (iv) an end portion that does not hybridize with the DNA target and is selected for its ability to enhance the fluorescence emission from the nanoclusters when in sufficient proximity to the nanoclusters.

In a preferred embodiment, the first portion of the nucleotide sequence of the DNA target is adjacent the second portion of the nucleotide sequence of the DNA target. The method also includes hybridizing the first strand and second strand to the nucleotide sequence of the target. Hybridization results in fluorescence emission from the nanoclusters of the probe. Furthermore, the first and second strands are positioned such that the end portion of the second strand selected for its ability to enhance fluorescence emission is in sufficient proximity to the nanoclusters in the first strand to enhance fluorescence emission from the nanoclusters. The method also includes detecting the enhanced fluorescence emission from the nanoclusters. In another preferred embodiment, the first portion of the nucleotide sequence of the DNA target is adjacent the second portion of the nucleotide sequence of the DNA target, and the first and second strand hybridize with the DNA target and also partially with each other to produce a stem. In embodiments with a stem, the fluorescence emission is significantly enhanced as the stem further induces proximity between the nanoclusters and the end portion of the second strand The invention also includes a duplex comprising:
  a target DNA,
  a first strand hybridized to the target DNA, the first strand having an unhybridized portion comprising silver nanoclusters, the silver nanoclusters having a fluorescence emission upon irradiation with UV light,
  a second strand hybridized to the target DNA, the second strand having an unhybridized end portion selected for enhancement of the fluorescence emission from the nanoclusters if it were in sufficient proximity to the nanoclusters, and
    wherein the silver nanoclusters from the first strand and the unhybridized end portion from the second strand are in sufficiently close proximity to each other for enhancement of the fluorescence emission of the silver nanoclusters

BRIEF DESCRIPTION OF THE SEQUENCE LISTING AND DRAWINGS

The present application contains a sequence listing in both paper and in computer readable format ("CRF"). The computer readable format is included on a compact disc having the name "118917 SL 2.17.11_ST25.txt" created 2.22.2011. The information recorded in computer readable format is identical to the written sequence listing. The content of the computer readable compact disc is hereby incorporated by reference. The accompanying drawings, which are incorporated in and form a part of the specification, illustrate the embodiments of the present invention and, together with the description, serve to explain the principles of the invention. In the drawings:

Figure 3A:
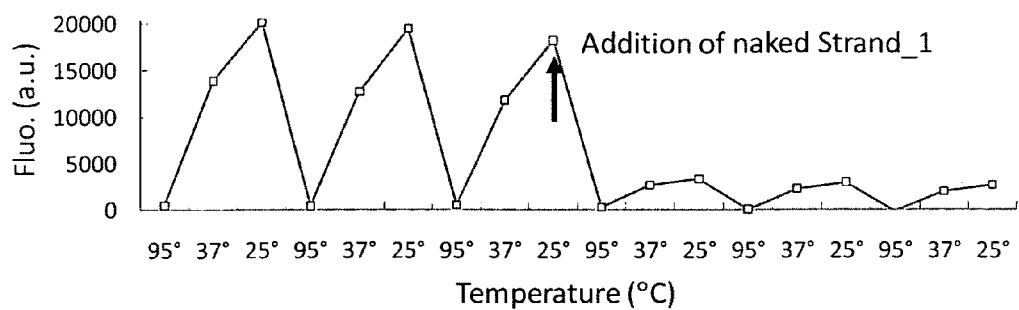
Figure 3B:
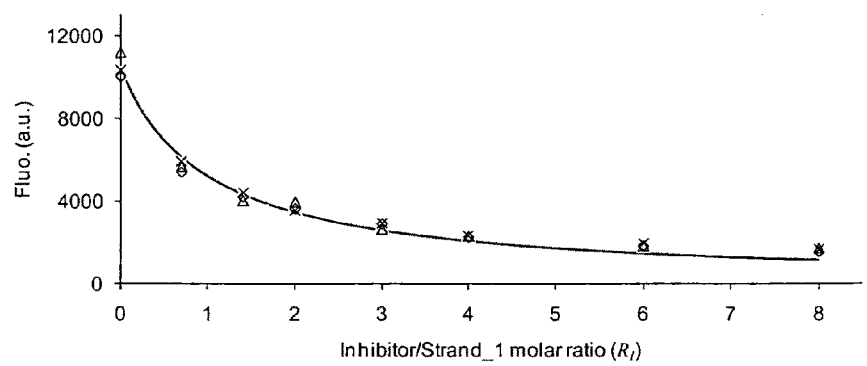

FIG. 3a shows a representative fluorescence trace of DNA/Ag NCs during a thermal cycling process. The sample initially contained a 1:1 molar ratio of nanocluster-bearing SEQ ID NO: 1 to SEQ ID NO: 12. A five-fold excess of naked (i.e. without nanoclusters) SEQ ID NO: 1 was spiked into the solution after three thermal cycles, as marked by the arrow. FIG. 3b shows a graph of fluorescence intensity versus inhibitor/Strand_1 (SEQ ID NO: 1) molar ratio. The inhibitor used here was Strand_HC (SEQ ID NO: 4). The gray line represents the equation of $I_0/(1+R_I)$, where $I_0$ is the no-inhibitor intensity and $R_1$ is the inhibitor/Strand_1 molar ratio. Markers (Δ, χ, o) represent three individual measurements.

Figure 4A:
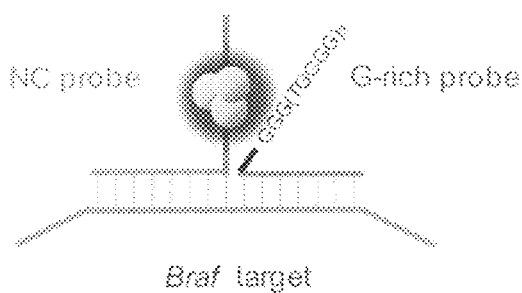
Figure 4B:
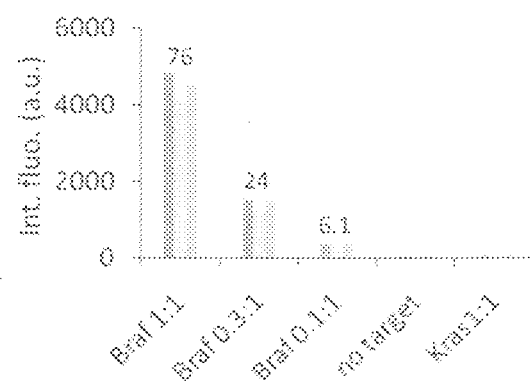

FIG. 4a shows a schematic image of an embodiment probe referred to as NanoCluster Beacon (NCB). FIG. 4b shows quantitative and specific detection of a target DNA of a nucleotide sequence from human Braf oncogene (SEQ ID NO: 18). Kras sequence (SEQ ID NO: 19) is from a human oncogene and was used as a non-specific control. "Braf 1:1" represents a sample with one to one target/probe ratio; in this case, both of them were at 7.5 µM. The averaged ratios of background-subtracted, integrated red fluorescence between three Braf samples and Kras 1:1 sample are listed above each bar. Red emission from sample without target and Kras sample were about the same. The nanocluster and G-rich probes used here were purified only by desalting during DNA synthesis. No purification was performed after nanocluster formation.

Figure 5A:
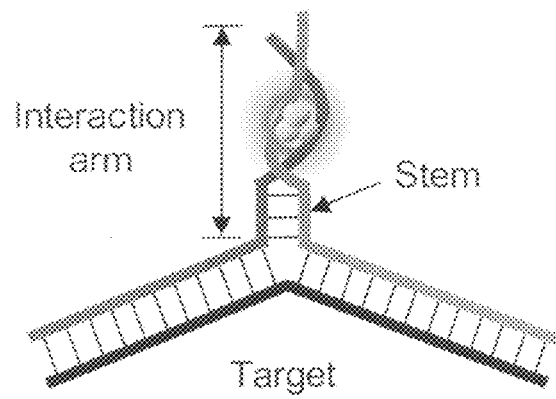
Figure 5B:
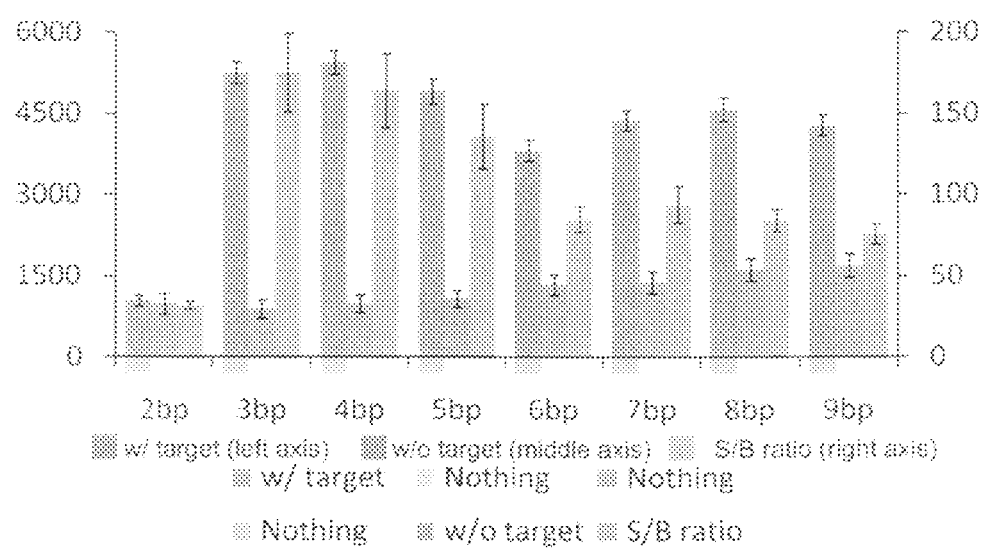

FIG. 5a shows a schematic of stem length optimization, and FIG. 5b shows integrated fluorescence with and without target, and S/B ratio at different stem length. A stem length of 3 base pairs gave the highest S/B ratio of 175.

DETAILED DESCRIPTION

This invention is concerned with probes and methods for DNA detection.

An embodiment includes a probe for detecting a target DNA. Another embodiment provides a method for detecting a target DNA. Yet another embodiment is a duplex formed upon hybridization of a probe of this invention with a target DNA.

An embodiment probe of this invention includes DNA-templated nanoclusters that emit red light when an unhybridized portion of the probe having guanine nucleotide bases is induced into proximity with the silver nanoclusters.

An embodiment probe of this invention includes DNA-templated nanoclusters that emit green light when an unhybridized portion of the probe having thymine nucleotide bases is induced into proximity with the silver nanoclusters.

This proximity condition occurs when the probe hybridizes with a target DNA. Prior to hybridization, the nanoclusters are only weakly fluorescent or nonfluorescent. After hybridization, the red (or green) fluorescence emission from the silver nanoclusters becomes greatly enhanced, i.e. the probes light up" upon hybridization with a target DNA because the nanoclusters are brought into proximity with guanine(s).

An embodiment that demonstrates the red fluorescence enhancement for a direct, quantitative and sensitive detection of a target DNA that is a human oncogene is provided. Probes of this invention for target DNA detection provide advantages over typical molecular beacons. For example, unlike molecular beacons, embodiment probes of this invention provide an enhancement in red (or green) emission from silver nanoclusters upon DNA recognition.

For demonstration purposes, probes were designed for hybridization with a target DNA from a human oncogene known as Braf gene, and also from Influenza Virus A. In these demonstration embodiments, significant fluorescence enhancements of templated silver nanoclusters were observed due to proximity to sequences including guanine(s).

Before describing probes of this invention, a more detailed description now follows that concerns the proximity effect of guanine nucleotide bases on the enhancement of red fluorescence emission of templated silver nanoclusters. A detailed description of this effect is best understood in combination with the accompanying FIGURES.

Figure 1A:
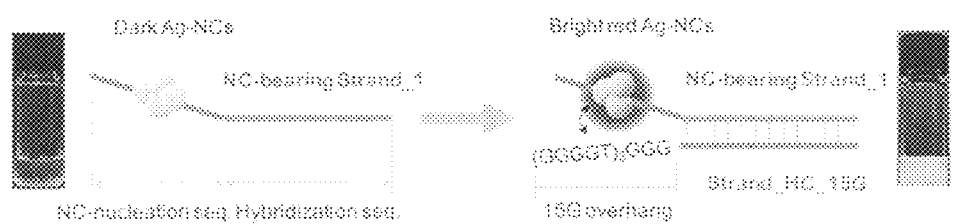
FIGS. 1a and 1b show schematic diagrams and plots that illustrate the effect of proximity of guanine nucleotide bases to templated silver nanoclusters.

FIG. 1a includes two schematic diagrams and two photographic images that illustrate the effect of proximity of guanine(s) on the red fluorescence emission of silver nanoclusters. The schematic diagram on the left shows silver nanoclusters ("Ag NCs") templated on the left side of a DNA strand referred to as Strand_1 (SEQ ID NO: 1; 5'-CCCT-TAATCCCCTATAATAAATTTTAAATATTATTTATTAAT-3'). SEQ ID NO: 1 is a 42 base sequence composed of a 12-base NC-nucleation portion called Strand_NC (SEQ ID NO: 3; 5'-CCCTTAATCCCC-3') designed by Richards et al. (see: Richards et al., "Oligonucleotide-Stabilized Ag Nanocluster Fluorescence," Journal of the American Chemical Society, April 2008, vol. 130, pp. 5038-5039, incorporated by reference) attached to a 30-base hybridization portion called Strand_H (SEQ ID NO: X, 5'-TATAATAAATTTTAAATAT-TATTTATTAAT-3').

The templated silver nanoclusters were formed on nucleation portion of SEQ ID NO: 1 using the protocol of Richie et al. (see: Richie et al. "Ag Nanocluster Formation Using a Cytosine Oligonucleotide Template," Journal of Physical Chemistry C, published online November 2006, vol. 111, pp. 175-181, incorporated by reference herein). SEQ ID NO: 1 was first dissolved in ultrapure deionized water. Ag NCs were formed by adding $AgNO_3$ (99.9%, SIGMA-ALDRICH) to the DNA solution, followed by reduction with $NaBH_4$. Final concentrations were 15 μM in SEQ ID NO: 1, 90 μM in $AgNO_3$, 90 μM in $NaBH_4$, and 20 mM in sodium phosphate buffer pH 6.6. The aqueous solution of $NaBH_4$ was prepared by dissolving the $NaBH_4$ powder in water and adding the required volume to the DNA/$Ag^+$ mixture within 30 sec. Eighteen hours after the initiation of NC nucleation the resulting Ag NCs had a weak green fluorescence emission. The schematic diagram at the left of FIG. 1a shows the strand is not yet hybridized to anything. The Ag NCs are referred "dark Ag-NCs". A photographic image near the diagram at the left of FIG. 1a is nearly opaque, indicating that the nanoclusters are only weakly fluorescent.

The schematic diagram at the right of FIG. 1a shows the effect of proximity of fifteen guanine nucleotide bases to the templated silver nanoclusters. This diagram shows nanocluster-bearing (i.e. NC-bearing) SEQ ID NO: 1 hybridized to a DNA strand referred to as Strand_HC_15G (SEQ ID NO: 12), which includes 15 guanine bases in an overhang portion. Hybridization of one strand to the other brings the templated silver nanoclusters in sufficient proximity to the guanine-rich overhang (SEQ ID NO: 20) of Strand_HC_15G (SEQ ID NO: 12). This proximity results in an enhancement in the red fluorescence emission of the nanoclusters after irradiating the nanoclusters with UV light. The photographic image near the schematic diagram on the right shows bright red fluorescence emission under UV (366 nm) irradiation.

Figure 1B:
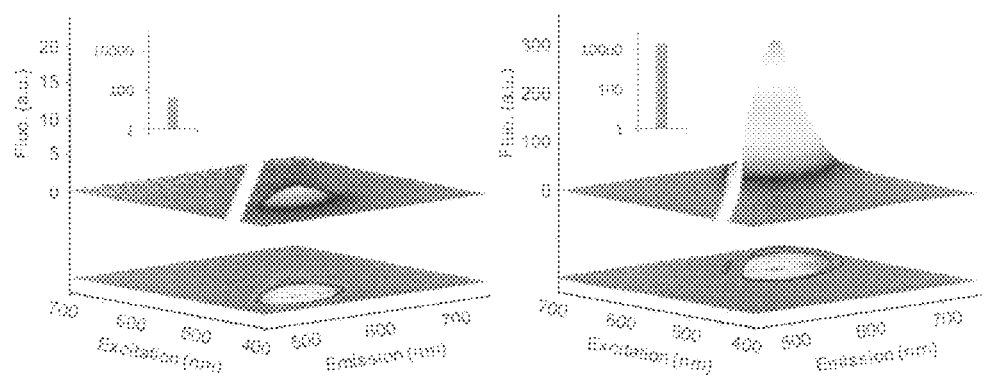

FIG. 1b includes 3D-contour plot and 2D-image plots of excitation/emission spectra corresponding to the left and right schematic diagrams of FIG. 1a. The insets show background-subtracted, integrated red fluorescence emission (595-800 nm, by 580 nm excitation) in a log scale. The excitation/emission peaks for aged NCs on Strand_HC_15G (SEQ ID NO: 12) before hybridization were at 460 nm/543 nm. The excitation/emission peaks changed to 580 nm/636 nm after hybridization. A comparison of the plots shows an enhancement in the red fluorescence emission of more than 500 fold. This red fluorescence emission enhancement is due to bringing the guanine rich overhand in proximity to the silver nanoclusters. This tremendous enhancement of red emission by bringing the nanoclusters into sufficient proximity to guanine(s) is an important aspect of the probe and method of this invention, which opens a new door to a new probe and type of gene detection.

Figure 2:
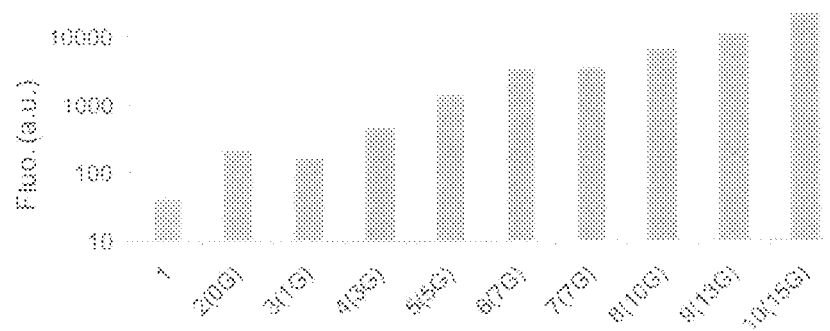
FIG. 2 shows a graphical representation of background-subtracted, integrated red fluorescence emission (595 nm-800 nm, by 580 nm excitation) from 10 samples with varying guanine content, and a table listing the complement used in each of the ten samples.

Experiments were conducted to examine fluorescence enhancement versus the number of guanines in proximity to silver nanoclusters. Nanocluster-bearing SEQ ID NO: 1 was hybridized with various complements (i.e. complementary DNA strands) having different amounts of guanine content in the overhang. A control experiment was also performed where the fluorescence emission of nanocluster-bearing SEQ ID NO: 1 was obtained in the absence of a complement. The relative fluorescence for this experiment was less than 100 in a.u. (arbitrary units). In separate experiments, nanocluster-bearing SEQ ID NO: 1 was hybridized with a strand containing 1 guanine in the overhang (SEQ ID NO: 6); 3 guanines in the overhang (SEQ ID NO: 7); 5 guanines in the overhang (SEQ ID NO: 6), 7 guanines in the overhang (SEQ ID NO: 9); 10 guanines in the overhang (SEQ ID NO: 10), 13 guanines in the overhang (SEQ ID NO: 11); and 15 guanines in the overhang (SEQ ID NO: 12). FIG. 2 shows a graph of the intensity of the red fluorescence from the silver nanoclusters after hybridization versus the number of guanine bases in the complementary strand. As the graph shows, the enhancement in red fluorescence was found to be highly dependent on the number of guanine bases in proximity of the Ag NCs caused by DNA hybridization. The molar concentrations of NC-bearing Strand_1 (SEQ ID NO: X) and the complement were both at 15 μM. The hybridization was carried out in a 20 mM sodium phosphate buffer at a pH of 6.6. The mixture was first heated up to 95° C. for one minute, followed by cooling down to room temperature for at least 50 minutes. Fluorescence was measured using a VARIAN CARY ECLIPSE Fluorescence Spectrophotometer.

A series of control experiments were performed to provide further support for the observed fluorescence enhancement being due to guanine proximity. Each and every complementary strand, by itself, failed to produce enhanced red emission. A strand consisting only of the nucleation sequence portion of SEQ ID NO: 1 failed to produce red emission. A strand consisting only of the hybridization sequence portion of SEQ ID NO: 1 also failed to produce red emission.

A gel-shift assay experiment proved the red emission came from a DNA duplex. The observation that the red fluorescence emission came from a duplex species was independently verified through measurements taken on a real-time PCR thermal cycler. The sample contained a 1:1 molar ratio of the nanocluster-bearing SEQ ID NO: 1 and SEQ ID NO: 12. FIG. 3a provides a graph of the data collected in fluorescence (arbitrary units) versus temperature in degrees Centigrade. The graph runs through several thermal cycles. The first cycle shown at beginning of the graph begins at a temperature of 95° C. where the fluorescence is lowest. As the temperature decreases, the fluorescence increases. To begin another cycle, the temperature is increased to 95° C., and the fluorescence decreases as the sample is brought to the higher temperature. Thus, the red fluorescence emission was large at low temperatures and small at high temperatures. One possible explanation for this behavior is that the Ag NCs at high temperature are weakly fluorescent species on single-stranded DNA, whereas at low temperature, where they are hybridized with complimentary DNA, they are bright due to proximity to guanine bases. To test this hypothesis, a five-fold excess of naked (i.e. non-NC-bearing) SEQ ID NO: 1 was added as an inhibitor. The arrow in the FIG. 3a shows when the excess SEQ ID NO: 1 was added. As FIG. 3a shows, the effect of adding the excess SEQ ID NO: 1 was the fluorescence recovered to approximately ⅙ of its original value at 25° C. In a separate competitive binding experiment, we spiked in another inhibitor, Strand_HC (SEQ ID NO: 4), which also prevented NC-bearing SEQ ID NO: 1 from complexing with SEQ ID NO: 12. As shown in FIG. 3b, the resulting red emission had a $1/(1+R_I)$ relationship with the amount of inhibitor used, where $R_I$ is the molar ratio between inhibitor and SEQ ID NO: 1. Results from all control experiments support a conclusion that the observed enhancement in red fluorescence from the nanoclusters was due to proximity of guanine bases.

In addition to testing fluorescence enhancement from guanine proximity, we explored possible fluorescence enhancement from the proximity of adenine, thymine, and cytosine bases. The proximity of other bases through DNA hybridization was tested, using the following DNA strand complements to SEQ ID NO: 1: Strand_HC_A12 (SEQ ID NO: 13), Strand_HC_T12 (SEQ ID NO: 14) and Strand_HC_C12 (SEQ ID NO: 15). SEQ ID NO: 13 had 13 adenines in the overhang after hybridization with SEQ ID NO: 1. SEQ ID NO: 14 had 12 thymines in the overhang after hybridization with SEQ ID NO: 1. SEQ ID NO: 15 had 12 cytosines in the overhang after hybridization with SEQ ID NO: 1. For cytosine, the measurements were complicated because cytosine-rich sequences can template NC formation and show red fluorescence. The adenine-rich and thymine-rich overhangs did not produce any red fluorescence enhancement of the nanoclusters. Hybridization with SEQ ID NO: 14 produced a green fluorescence from the nanoclusters.

We do not fully understand the underlying mechanism for this guanine proximity-based fluorescence enhancement. Studies have reported on the interactions between guanine bases and some commonly used organic dyes, such as fluoroscein, Rhodamine derivatives, BODIPY FL, oxazine, Cy5, and coumarin. In most cases, but not all, guanine-dye interactions led to fluorescence quenching of excited fluorophores. Believed to be a photoinduced charge transfer phenomenon, guanine-mediated fluorescence quenching has been studied systematically on a variety of DNA sequences and structures. Guanine is the nucleobase having the lowest oxidation potential (1.49 V), therefore, depending on the excited-state reduction potential of the fluorophores, guanine bases can donate electrons to nearby fluorophores, quenching their fluorescence. Charge transfer between nucleobases and Ag NCs has been recently reported to lead to a long-lived, charge-separated trap state that causes fluorescence intermittency (i.e. blinking) of Ag NCs on microsecond time scale. In our case, it is possible that guanine bases serve as electron donors and reducing agents, which convert the oxidized NC species (in this case, weakly emissive NCs) into the reduced ones (bright red-emitting NCs). A second possibility for the observed phenomenon is that the secondary structures that G-rich sequences form (i.e. G-quadraplex) may change the ligand environment of the Ag NC, in this case, favoring the formation of the red-emitting NCs. The influence of DNA secondary structure on the yield and fluorescence wavelength of Ag NCs has been reported. A remarkable spectrum shift was seen for G-rich sequences with and without the capability to form secondary structures. A third possibility is that the conformation change of DNA due to cytosine-guanine base-pairing may lead to the dissociation of non-emissive NCs and the formation of red-emitting ones, much like the way that sodium chloride converts the oxidized NCs into reduced ones. A problem with this hypothesis is that the DNA strand that is a perfect complement to SEQ ID NO: 1 (Strand_1C, SEQ ID NO: 5; which has 7G in its overhang) did not give the highest red fluorescence enhancement. The simple trend of increased emission with an increase in the number of guanine bases in proximity may imply charge transfer to be the mechanism responsible for the observed phenomenon, as more electron donors are present. However, similar low-level fluorescence enhancement was observed when each of the four kinds of dNTP was individually spiked into solution containing aged NCs on SEQ ID NO: 1 (final concentration 50 mM). This result contradicted prior reports on guanine-mediated quenching of organic dyes (such as BODIPY FL) due to photoinduced charge transfer, where only guanine quenches. While the concentration used (50 mM) is adequate to induce dynamic quenching, the local concentration of nucleotides around the NCs is still orders of magnitude below the effective concentration generated by proximity through hybridization. We are still working towards a better understanding of the mechanism for the observed fluorescence enhancement.

Although the underlying mechanism for fluorescence enhancement of silver nanoclusters by proximity to guanine is not yet completely understood, we took advantage of this enhancement effect and designed a probe for detecting a target DNA. The probe "lights up" when it hybridizes to a specific target DNA. Lighting up is the signal that the probe has hybridized to the target DNA. We named these probes "NanoCluster Beacons" (NCBs).

Thus, the invention is concerned with probes for detecting a target DNA. The DNA target has nucleotide sequence. The probe includes a first strand and a second strand. The first strand includes a nucleotide sequence that complements, and can hybridize with, a first portion of the nucleotide sequence of the DNA target. The first strand also includes an end portion that does not hybridize with the DNA target and comprises templated fluorescent metal nanoclusters. The second strand of the probe includes a nucleotide sequence that complements, and can hybridize with, a second portion of the nucleotide sequence of the DNA target. The second strand also includes an end portion that does not hybridize with the DNA target and comprises at least one guanine. Upon hybridizing the first and second strands of the probe to the DNA target, the at least on guanine is brought into sufficient proximity to the nanoclusters to enhance fluorescence emission from the nanoclusters.

The invention is also concerned with a method for target DNA detection. The method includes providing a DNA target comprising a nucleotide sequence and providing a fluorescent probe for detecting the DNA target. The probe includes a first strand and a second strand. The first strand has a nucleotide sequence portion that complements, and can hybridize with, a first portion of the nucleotide sequence of the DNA target. The first strand also has end portion that does not hybridize with the DNA target and comprises templated fluorescent metal nanoclusters. The second strand has a nucleotide sequence portion that complements, and can hybridize with, a second portion of the nucleotide sequence of the DNA target, and an end portion that does not hybridize with the DNA target and is selected for its ability to enhance the fluorescence emission of the nanoclusters when in sufficiently close proximity to the nanoclusters. The method also includes hybridizing the first strand and second strand to the nucleotide sequence of the target. Hybridization results in fluorescence emission from the nanoclusters of the probe. Furthermore, the first and second strands are positioned such that the unhybridized end portion of the second strand is in sufficient proximity to the nanoclusters in the first strand to enhance fluorescence emission from the nanoclusters. The method also includes detecting the enhanced fluorescence emission from the nanoclusters.

The invention also includes a duplex that forms when a probe of this invention hybridizes with a target DNA. The duplex also includes a first strand hybridized to the target DNA, the first strand having an unhybridized portion comprising an oligonucleotide comprising at least one guanine. The duplex also includes a second strand hybridized to the target DNA, the second strand having an unhybridized portion comprising silver nanoclusters, the silver nanoclusters having a fluorescence emission, the silver nanoclusters and the at least one guanine being in sufficiently close proximity to each other for enhancement of the red fluorescence emission of the silver nanoclusters.

FIG. 4 shows a schematic representation of an embodiment probe of this invention hybridized to a target DNA. As FIG. 4 shows, the probe (i.e. NanoCluster Beacon) includes two short linear DNA strands. One of the strands is labeled NC probe (SEQ ID NO: 16). This is the nanocluster-bearing strand portion of the probe. In the embodiment shown in FIG. 4, the other strand is labeled G-rich probe (SEQ ID NO: 17). SEQ ID NO: 17 is the portion of this embodiment probe with the at least one guanine that influences the fluorescence emission of the nanoclusters after both strands of the probe hybridize with the target DNA. As the FIGURE shows, both strands are hybridized to a target DNA, and the guanines are in sufficient proximity to the nanoclusters to influence them by enhancement of red fluorescence emission from the nanoclusters upon UV irradiation.

It should be understood that this invention is not limited to any particular target DNA. Any DNA strand can be detected once a nucleotide sequence specific for that DNA strand is known. A probe of this invention can then be designed with two strands, each having a portion that can hybridize to the target DNA. The strands are designed for hybridization to a specific sequence. A portion of each strand hybridizes to the target DNA such that the nanoclusters on one strand, after hybridization, are in sufficient proximity to the guanine in the overhang of the second strand, to produce the enhancement in fluorescence. In a non-limiting embodiment that demonstrates the probe and method and the enhancement in fluorescence, a 76-fold stronger red emission was seen in the presence of target DNA SEQ ID NO: 18 from human Braf gene as compared to the sample without target DNA or with non-specific target, using only un-optimized probe design. The probe included a 36-base DNA strand called nanocluster-bearing probe_1 (SEQ ID NO: 26) and a 39 base long, guanine-rich DNA strand called G-rich probe_1 (SEQ ID NO: 27).

To directly compare NanoCluster Beacon performance with that for a molecular beacon, we designed another Nano-Cluster Beacon to detect an influenza target (a sequence from Influenza A virus (S-OIV) (H1N1). The target sequence was SEQ ID NO: 28. This second embodiment of the Nanocluster Beacon probe (NCB_2) included a 40-base long strand called nanocluster-bearing probe_2 (SEQ ID NO: 29) and a 45 base long, guanine-rich strand G-rich probe_2 (SEQ ID NO: 30). We achieved a signal to background ratio (S/B) of 175 with the NCB_2 versus a S/B ratio of 32 for the molecular beacon on the same target.

Benefits of using NCBs of the present invention include simple preparation, low cost, and high yield. In contrast to linear hybridization probes (such as those in fluorescence-in-situ-hybridization, FISH, assays), there are no added purification steps. In FISH-type assays, some purification to remove excess dye is always required for making any dye-labeled DNA probe, adding cost. For the NCB probe and target DNA detection method demonstrated here, there is no need to remove excess silver ions from solution (silver ions were used to prepare the nanoclusters) because silver ions are essentially non-fluorescent. Furthermore, because unhybridized NCBs are relatively dark, there is no need to wash away or quench unbound probes, which is not the case for known, standard linear hybridization probes. In contrast to molecular beacons, NCBs offer distinct advantages. For molecular beacons, removal of nonfunctional beacons (e.g. beacons only labeled with a dye but not a quencher) is necessary because they can be fluorescent regardless of conformation. By contrast, no such purification is needed with an NCB probe of the present invention.

We studied the interactions between DNA-templated fluorescent silver nanoclusters and nearby guanine bases. Fluorescence quenching by guanine due to photoinduced charge transfer has been reported for many widely used organic dyes. In contrast, we found that for red- and infrared-emitting fluorescent Ag nanoclusters formed on DNA templates, interactions with nearby guanine bases tended to protect these NCs against oxidation, making them brighter, and more stable in aqueous solution.

Nanoclusters formed in the absence of guanine-rich DNA changed from a red-emitting reduced nanoclusters into a green-emitting oxidized species in a few hours in air-saturated solutions. By contrast, when guanine bases were brought close to NCs, through DNA hybridization, guanine served as an electron donor and reducing agent, which prevented the Ag NCs from being quickly oxidized in air-saturated solutions, increasing the stability from hours to days. In addition, hybridization with guanine-rich DNA could be used to reduce the already oxidized NCs back to the red-emitting reduced ones. Single-stranded DNA templates were also designed with a nanocluster formation sequence and a guanine-rich sequence at each end. Similarly, we found that the guanine-rich end portion helped stabilize the fluorescence of the red-emitting NC fluorophores, in comparison to single-stranded templates with only cluster formation sequences but no guanine-rich end portions. Using this strategy, a DNA sequence has been designed that produces highly emissive Ag NC fluorophores with an extended shelf life. This sequence is useful in a variety of biological applications, including fluorescence imaging and biosensing.

Red fluorescence emission can be triggered from guanine proximity to DNA/Ag NCs by DNA hybridization, which was used for the demonstration of a new type of DNA detection probe, the NanoCluster Beacon. The NanoCluster Beacon includes two strands that are designed to bind in juxtaposition to a target DNA, allowing guanine bases on one probe to interact with non-fluorescent nanoclusters on the other probe, transforming those non-fluorescent nanoclusters into bright red-emitting clusters. Here, the use of a NanoCluster Beacon for the detection of an oncogene in a solution assay has been demonstrated. Other applications of the tremendous fluorescence enhancement enabled by guanine proximity include DNA micro-arrays, and sensitive and selective labeling for fluorescence microscopy. The probe may be used to detect a specific DNA target in a manner that circumvents many of the shortcomings of conventional molecular beacons ("MBs").

NCBs have the potential to reach an ultrahigh signal-to-background (SB) ratio in molecular sensing. Since the fluorescence enhancement is caused by intrinsic nucleobases, our detection technique is simple, inexpensive, and compatible with commercial DNA synthesizers. While NCBs are clearly promising as future probes in quantitative biology, their design rules have yet been addressed.

In another embodiment of the invention, the dark nanoclusters templated on a strand can be lit up into three distinct colors (green, yellow/orange, and red) by employing different proximal sequences, potentially enabling the use of NCBs in multiplexed assays.

We also tested different nanocluster-nucleation sequences and found the sequences that created strong red fluorescence enhancement share a common 5'-$C_3$NNNNN$C_4$ motif, where N is either a thymine (T) or an adenine (A) base.

We optimized the design of NCBs by testing the effect of different lengths of an interaction stem. The highest signal-to-background (SB) ratio of 175, a factor of 5 better than conventional molecular beacons, was achieved when the stem length was 3 base pairs long.

With the exception of target DNA strands (i.e. SEQ ID NO: 18, SEQ ID NO: 19, and SEQ ID NO: 28), all other DNA strands are artificial sequences that were purchased from Integrated DNA Technologies Incorporated and were purified by desalting. DNA/Ag NCs were made using the protocol developed by Ritchie et al. (vide supra). NC-bearing strand was first dissolved in ultrapure deionized water. Silver nanoclusters were formed by adding $AgNO_3$ (99.9%, Sigma-Aldrich) to the DNA solution, followed by reduction with sodium borohydride. Final concentrations were 15 µM in DNA strand, 90 µM in $AgNO_3$, and 90 µM in $NaBH_4$ in 20 mM pH 6.6 sodium phosphate buffer. The aqueous solution of $NaBH_4$ was prepared by dissolving $NaBH_4$ powder in water and adding the required volume to the DNA/$Ag^+$ mixture within 30 seconds, followed by vigorous shaking for 5 seconds. The reaction was kept in the dark at room temperature for 18 hours before use.

Fluorescence was measured using a VARIAN CARY ECLIPSE Fluorescence Spectrophotometer. The images of samples were acquired by a digital camera while the samples were placed on a gel imager (INGENIUS, SYNGENE).

An important feature of NCBs is that dark Ag NCs on a DNA motif can be lit up into distinct colors, creating a complementary palette. This is achieved by bringing different DNA sequences (i.e. proximal sequences) into proximity of the originally dark Ag NCs (templated on a 5'-$C_3$TTAAT$C_4$ motif). Three distinct light-up colors (green, yellow/orange, and red) were obtained by employing three different proximal sequences. This important characteristic, having multiple light-up colors from the same origin, is not commonly shared by organic dyes or semiconductor quantum dots, opening opportunities for NCBs in multiplexed assays.

After investigating the magnitude of fluorescence enhancement created by proximal sequences of varying guanine content a further investigation was conducted for red fluorescence enhancement by testing NC-bearing DNA strands having an identical hybridization sequence but different NC-nucleation sequences. Six strands were tested. They were Strand_1 (SEQ ID NO: 1), Strand_2 (SEQ ID NO: 21), Strand_3 (SEQ ID NO: 22), Strand_4 (SEQ ID NO: 23), Strand_5 (SEQ ID NO: 24), and Strand_6 (SEQ ID NO: 25). SEQ ID NO: 1, SEQ ID NO: 2, and SEQ ID NO: 3 were described in Richards et al. (vide infra) SEQ ID NO: 4 was described in Ritchie et al. "Ag nanocluster formation using a cytosine oligonucleotide template," *Journal of Physical Chemistry C*, vol. 111, no. 1, pp. 175-181, 2007, incorporated by reference. SEQ ID NO: 5 and SEQ ID NO: 6 were described in Nazarenko et al. "Effect of primary and secondary structure of oligodeoxyribonucleotides on the fluorescent properties of conjugated dyes," *Nucleic Acids Research*, vol. 30, no. 9, pp. 2089-2095, 2002, incorporated by reference.

Strong red fluorescence emission after hybridization was seen from three sequences share a common 5'-$C_3$NNNNN$C_4$ motif ("MOTIF"), where N is either a thymine (T) or an adenosine (A) base. The emission spectra of all the six samples changed in some ways after hybridization—either from nearly no fluorescence to a strong emission (e.g. SEQ ID NO: 1) or from one color to another (SEQ ID NO: 23 and SEQ ID NO: 24). This characteristic leads to the possibility of creating NCBs with a variety of color-change scenarios upon target recognition, which will enrich our fluorescence detection tool box in the near future. The guanine N7 site plays a critical role in the observed red fluorescence enhancement.

The design of NCB can be optimized by allowing the strand with templated nanoclusters and the strand with the guanine-containing overhang to form a short "stem" on the NCB interaction arm (FIG. 5a). Such a short stem helps to bring the nucleation sequence closer to the proximal sequence, resulting in tighter interactions. As a consequence, the light-up emission is enhanced. As shown in FIG. 5b, target-specific fluorescence increased with increasing stem length up to 4 base pairs, but background fluorescence continued to grow beyond that. The highest S/B ratio, 175, was achieved when the stem was 3 base pairs long, which is five times better than the S/B ratio obtained by the stem length of 2 base pairs.

It is possible that guanine bases serve as electron donors, converting oxidized-NC species (in this case, non-emissive NCs) into reduced-NC species (bright red-emitting NCs). To prove this electron-transfer hypothesis, a proximal sequence rich of 7-deazaguanines, which are stronger electron donors than guanines was made and tested. Surprisingly, we found no light-up effect from such a deazaguanine-rich proximal sequence, weakening the electron transfer hypothesis. Another experimental result that weakens the electron-transfer hypothesis is that thymine proximity produced a green fluorescence enhancement, while adenine proximity did not generate any measurable fluorescence enhancement, with thymine being a worse electron donor than adenine. The only difference between guanine and 7-deazaguanine is the nitrogen atom at the guanine N7 site (in 7-deazaguanine, it is replaced with a CH group). It was previously reported that the guanine N7 site may be the primary location for silver attachment to a DNA duplex (see: Gwinn et al., "Sequence-dependent fluorescence of DNA-hosted silver nanoclusters, Advanced Materials, vol. 20, no. 2, pp. 279-283, 2008, incorporated by reference). Our 7-deazaguanine experiment indicates that the guanine N7 site plays a critical role in the observed red fluorescence enhancement.

We demonstrated controlled conversion of DNA/Ag NCs between bright and dark states and, based upon this finding, designed a new molecular probe, NanoCluster Beacon, for homogeneous detection of nucleic acid targets. Not relying on Förster energy transfer as the fluorescence on/off switching mechanism, NCBs have the potential to reach an ultrahigh signal-to-background (S/B) ratio in molecular sensing. The fluorescence enhancement is caused by intrinsic nucleobases. Therefore, the probe and method for target DNA detection is simple, inexpensive, and compatible with commercial DNA synthesizers. We also demonstrated a palette of NCB light-up colors can be produced from the same origin by employing different proximal sequences. The nanocluster-nucleation sequences capable of achieving strong red fluorescence enhancement share a common 5'-$C_3$NNNNN$C_4$ motif.

Although the present invention has been described with reference to specific details, it is not intended that such details should be regarded as limitations upon the scope of the invention, except as and to the extent that they are included in the accompanying claims.

Names and Sequences of the Oligonucleotides:

```
Name: Strand_1
Sequence:
                                              [SEQ ID NO: 1]
5'-CCCTTAATCCCCTATAATAAATTTTAAATATTATTTATTAAT-3'
Length: 42
```

Artificial Sequence

Comment: Synthetic DNA sequence composed of a 12 base nanocluster nucleation portion called Strand_NC designed by Richards et al. and a 30 base hybridization portion called Strand_H

```
Name: Strand_H
Sequence:
                                              [SEQ ID NO: 2]
5'-TATAATAAATTTTAAATATTATTTATTAAT-3'
Length: 30
```

Artificial Sequence

Comment: Synthetic DNA sequence that is the 30 base hybridization portion of Strand_1

```
Name: Strand_NC
Length: 12
      Sequence: 5'-CCCTTAATCCCC-3' [SEQ ID NO: 3]
```

Artificial Sequence

Comment: Synthetic DNA sequence that is the 12 base nanocluster nucleation portion of Strand_1

```
Name: Strand_HC
Length: 30
Sequence:
5'-ATTAATAAATAATATTTAAAATTTATTATA-3'   [SEQ ID NO: 4]
```

Artificial Sequence

Comment: Synthetic DNA sequence spiked as an inhibitor to prevent SEQ ID NO: 1 from complexing to SEQ ID NO: 12

```
Name: Strand_1C
Length: 42
Sequence:
                                              [SEQ ID NO: 5]
5'-AATAATAAATAATATTTAAAATTTATTATAGGGGATTAAGGG-3'
```

Artificial Sequence

Comment: Synthetic DNA sequence that is a perfect complement to SEQ ID NO: 1

```
Name: Strand_HC_1G
Length: 31
Sequence:
                                              [SEQ ID NO: 6]
     5'-ATTAATAAATAATATTTAAAATTTATTATAG-3'
```

Artificial Sequence

Comment: Synthetic DNA strand having 1 guanine in the overhang after it hybridizes with SEQ ID NO: 1

```
Name: Strand_HC_3G
Length: 33
Sequence:
                                              [SEQ ID NO: 7]
5'-ATTAATAAATAATATTTAAAATTTATTATAGGG-3'
```

Artificial Sequence

Comment: Synthetic DNA strand having 3 guanines in the overhang after it hybridizes with SEQ ID NO: 1

```
Name: Strand_HC_5G
Length: 36
Sequence:
                                              [SEQ ID NO: 8]
5'-ATTAATAAATAATATTTAAAATTTATTATAGGGTGG-3'
```

Artificial Sequence

Comment: Synthetic DNA strand having 5 guanines in the overhang after it hybridizes with SEQ ID NO: 1

```
Name: Strand_HC_7G
Length: 38
Sequence:
                                              [SEQ ID NO: 9]
5'-ATTAATAAATAATATTTAAAATTTATTATAGGGTGGGG-3'
```

Artificial Sequence

Comment: Synthetic DNA strand having 7 guanines in the overhang after it hybridizes with SEQ ID NO: 1

```
Name: Strand_HC_10G
Length: 42
Sequence:
                                              [SEQ ID NO: 10]
5'-ATTAATAAATAATATTTAAAATTTATTATAGGGTGGGTGGG-3'
```

Artificial Sequence

Comment: Synthetic DNA strand having 10 guanines in the overhang after it hybridizes with SEQ ID NO: 1

```
Name: Strand_HC_13G
Length: 46
Sequence:
                                              [SEQ ID NO: 11]
5'-ATTAATAAATAATATTTAAAATTTATTATAGGGTGGGTGGGTG
GG-3'
```

Artificial Sequence

Comment: Synthetic DNA strand having 13 guanines in the overhang after it hybridizes with SEQ ID NO: 1

```
Name: Strand_HC_15G
Length: 48
Sequence:
                                              [SEQ ID NO: 12]
5'-ATTAATAAATAATATTTAAAATTTATTATAGGGTGGGTGGGGT
GGGG-3'
```

Artificial Sequence

Comment: Synthetic DNA strand having 15 guanines in the overhang after it hybridizes with SEQ ID NO: 1

Name: Strand_HC_A12
Length: 42
Sequence:
[SEQ ID NO: 13]
5'-ATTAATAAATAATATTTAAAATTTATTATAAAAAAAAAAAA-3'
Artificial Sequence
Comment: Synthetic adenine-rich DNA strand, has 12 adenines in the overhang after it hybridizes with SEQ ID NO: 1

Name: Strand_HC_T12
Length: 42
Sequence:
[SEQ ID NO: 14]
5'-ATTAATAAATAATATTTAAAATTTATTATATTTTTTTTTTTT-3'
Artificial Sequence
Comment: Synthetic thymine rich DNA strand, has 12 thymines in the overhang after it hybridizes with SEQ ID NO: 1

Name: Strand_HC_C12
Length: 42
Sequence:
[SEQ ID NO: 15]
5'-ATTAATAAATAATATTTAAAATTTATTATACCCCCCCCCCCC-3'
Artificial Sequence
Comment: Synthetic cytosine-rich DNA strand, has 12 cytosines in the overhang after it hybridizes with SEQ ID NO: 1

Name: NC probe
Length: 36
Sequence:
[SEQ ID NO: 16]
5'-CCCTTAATCCCCTGTAGCTAGACCAAAATCACCTAT-3'
Artificial Sequence
Comment: Synthetic DNA strand that is the nanocluster-bearing portion of a NanoCluster Beacon probe embodiment Name: G-rich probe
Length: 39
Sequence:
[SEQ ID NO: 17]
5'-CCCACTCCATCGAGATTTCACGGGTGGGGTGGGGTGGGG-3'
Artificial Sequence
Comment: Synthetic DNA strand that is the guanine-rich portion of a NanoCluster Beacon probe embodiment Name: Braf target
Length: 80
Sequence:
[SEQ ID NO: 18]
5'-AGACCTCACAGTAAAAATAGGTGATTTTGGTCTAGCTACAGTG AAATCTCGATGGAGTGGGTCCCATCAGTTTGAACAGT-3'
Homo Sapiens Name: Kras target
Length: 80
Sequence:
[SEQ ID NO: 19]
5'-TGAAAATGACTGAATATAAACTTGTGGTAGTTGGAGCTGGTGG

CGTAGGCAAGAGTGCCTTGACGATACAGCTAATTCAG-3'

Name: Overhang_15G
Length: 18
Sequence:
5'-GGGTGGGGTGGGGTGGGG-3'   [SEQ ID NO: 20]
Artificial Sequence
Comment: Synthetic DNA sequence that is the G-rich overhang of SEQ ID NO: 12 after hybridization Name: Strand_2
Length: 42
Sequence:
[SEQ ID NO: 21]
5'-CCCTTTAACCCCTATAATAAATTTTAAATATTATTTATTAAT-3'
Artificial Sequence
Comment: Synthetic nanocluster-bearing DNA strand Name: Strand_3
Length: 42
Sequence:
[SEQ ID NO: 22]
5'-CCTCCTTCCTCCTATAATAAATTTTAAATATTATTTATTAAT-3'
Artificial Sequence
Comment: Synthetic nanocluster-bearing DNA strand Name: Strand_4
Length: 42
Sequence:
[SEQ ID NO: 23]
5'-CCCCCCCCCCCCCTATAATAAATTTTAAATATTATTTATTAAT-3'
Artificial Sequence
Comment: Synthetic nanocluster-bearing DNA strand Name: Strand_5
Length: 42
Sequence:
[SEQ ID NO: 24]
5'-CCCTATAACCCCTATAATAAATTTTAAATATTATTTATTAAT-3'
Artificial Sequence
Comment: Synthetic nanocluster-bearing DNA strand Name: Strand_6
Length: 42
Sequence:
[SEQ ID NO: 25]
5'-CCCTAACTCCCCTATAATAAATTTTAAATATTATTTATTAAT-3'
Artificial Sequence
Comment: Synthetic nanocluster-bearing DNA strand Name: nanocluster-bearing probe_1
Length: 36
Sequence:
[SEQ ID NO: 26]
5'-CCCTTAATCCCCTGTAGCTAGACCAAAATCACCTAT-3'
Artificial Sequence
Comment: Synthetic 36-base DNA strand, nanocluster bearing portion of probe for detecting Braf oncogene Name: G-rich probe_1
Length: 39
Sequencer:
[SEQ ID NO: 27]
5'-CCCACTCCATCGAGATTTCACGGGTGGGGTGGGGTGGGG-3'

Artificial Sequence

Comment: Synthetic 39 base DNA strand, guanine-rich portion of probe for detecting Braf oncogene Name: H1N1 target
Length: 60
Sequence:
[SEQ ID NO: 28]
5'-TTTGGGTCTTATTGCTATTTCCGGCTTGAACTTCTTGCTGTATCTTGATGACCCCACAAA-3'

Influenza A Virus

Name: nanocluster-bearing probe_2
Length: 40
Sequence:
[SEQ ID NO: 29]
5'-CCCTTAATCCCCTATTTCAAGCGGGAAATAGCAATAAGAC-3'

Artificial Sequence

Comment: Synthetic 40 base DNA strand, nanocluster-bearing portion of probe for detecting Influenza A virus Name: G-rich probe_2
Length: 45
Sequence:
[SEQ ID NO: 30]
5'-GGGTCATCAAGATACAGCAAGAAGATAGGGTGGGGTGGGGTGGGG-3'

Artificial Sequence

Comment: Synthetic 45 base DNA strand, guanine-rich portion of probe for detecting Influenza A virus Name: MOTIF
Length: 12
Sequence:
5'-CCCNNNNNCCCC-3'   [SEQ ID NO: 31]

Artificial Sequence

Comment: Synthetic DNA sequence

Misc_Feature: N may be adenine or thymine,

---

What is claimed is:

1. A probe for detecting a target DNA having a nucleotide sequence, the probe comprising:
   a first strand having
   (i) a nucleotide sequence that complements, and can hybridize with, a first portion of the nucleotide sequence of the DNA target,
   (ii) an end portion nucleotide sequence that does not hybridize with the DNA target and comprises templated fluorescent metal nanoclusters, and
   and a second strand having
   (iii) a nucleotide sequence that complements, and can hybridize with, a second portion of the nucleotide sequence of the target DNA, and
   (iv) an end portion nucleotide sequence that comprises a sequence that does not hybridize with the target DNA target and would enhance the fluorescence emission from the nanoclusters if it were in sufficient proximity to the nanoclusters,
   wherein upon hybridizing the first strand and second strand of the probe to the target DNA, the proximity of the end portion of the second strand enhances the fluorescence emission from the nanoclusters.

2. The probe of claim 1, wherein said first portion of said DNA target is adjacent said second portion of said DNA target.

3. The probe of claim 2, wherein at least a portion of the first strand hybridizes with a portion of the second strand to form a stem, which improves the proximity of the nanoclusters to the unhybridized end portion of the second strand to further enhance the fluorescence emission from the nanoclusters.

4. The probe of claim 2, wherein the end portion nucleotide sequence of the second strand includes a number of guanines selected from one, three, five, seven, ten, thirteen, and fifteen, wherein the end portion enhances red fluorescence emission, or wherein the end portion nucleotide sequence of the second strand includes thymines and no guanine and enhances green fluorescence emission.

5. The probe of claim 4, wherein the probe provides an enhanced red fluorescence emission that increases as the number of guanines increases.

6. The method of claim 1, wherein the first nucleotide sequence and the second nucleotide sequence of the DNA target are adjacent.

7. The method of claim 1, wherein the enhanced fluorescence emission is red fluorescence emission.

8. The method of claim 1, wherein the enhanced fluorescence emission is green fluorescence emission.

9. The method of claim 1, wherein the enhanced fluorescence emission is yellow/orange fluorescence emission.

10. A method for detecting a DNA target, comprising:
    providing a DNA target comprising a first nucleotide sequence and a second nucleotide sequence near the first nucleotide sequence,
    providing a probe for detecting the DNA target, the probe including a first strand having
    (i) a nucleotide sequence portion that complements, and can hybridize with, the first nucleotide sequence of the DNA target,
    (ii) an end portion that does not hybridize with the DNA target and comprises templated fluorescent metal nanoclusters,
    and a second strand having
    (iii) a nucleotide sequence portion that complements, and can hybridize with, the second nucleotide sequence of the DNA target, and
    (iv) an end portion that does not hybridize with the DNA target and would enhance the fluorescence emission from the nanoclusters if it were in sufficient proximity to the nanoclusters, hybridizing the first strand of the probe to the first nucleotide sequence of the DNA target and hybridizing the second strand of the probe to the second nucleotide sequence of the DNA target, which results in fluorescence emission from the nanoclusters, furthermore wherein hybridization results in the end portion of the second strand being in sufficient proximity to the nanoclusters to further enhance fluorescence emission from the nanoclusters, and detecting the enhanced fluorescence emission.

11. A duplex comprising:

a target DNA;

a first strand comprising a first portion hybridized to the target DNA and a second portion not hybridized to the target DNA and comprising an oligonucleotide sequence having at least one guanine, and a second strand comprising a first portion hybridized to the target DNA and a second portion not hybridized to the target DNA and comprising silver nanoclusters, wherein the second portion of the first strand is in sufficiently close proximity to the silver nanoclusters to enhance the fluorescence emission of the silver nanoclusters.

12. The duplex of claim 11, wherein the fluorescence emission comprises red fluorescence emission.

* * * * *

SEQUENCE LISTING

```
<160> NUMBER OF SEQ ID NOS: 31

<210> SEQ ID NO 1
<211> LENGTH: 42
<212> TYPE: DNA
<213> ORGANISM: Artificial Sequence
<220> FEATURE:
<223> OTHER INFORMATION: Synthetic DNA sequence composed of a 12 base
      nanocluster nucleation portion called Strand_NC designed by
      Richards et al. and a 30 base hybridization portion called
      Strand_H

<400> SEQUENCE: 1
cccttaatcc cctataataa attttaaata ttatttatta at                         42

<210> SEQ ID NO 2
<211> LENGTH: 30
<212> TYPE: DNA
<213> ORGANISM: Artificial Sequence
<220> FEATURE:
<223> OTHER INFORMATION: Synthetic DNA sequence that is the 30 base
      hybridization portion of Strand_1

<400> SEQUENCE: 2
tataataaat tttaaatatt atttattaat                                       30

<210> SEQ ID NO 3
<211> LENGTH: 12
<212> TYPE: DNA
<213> ORGANISM: Artificial Sequence
<220> FEATURE:
<223> OTHER INFORMATION: Synthetic DNA sequence that is the 12 base
      nanocluster nucleation portion of Strand_1

<400> SEQUENCE: 3
cccttaatcc cc                                                          12

<210> SEQ ID NO 4
<211> LENGTH: 30
```

```
<212> TYPE: DNA
<213> ORGANISM: Artificial Sequence
<220> FEATURE:
<223> OTHER INFORMATION: Synthetic DNA sequence spiked as an inhibitor
      to prevent SEQ ID NO: 1 from complexing to SEQ ID NO: 12

<400> SEQUENCE: 4
attaataaat aatatttaaa atttattata                                    30

<210> SEQ ID NO 5
<211> LENGTH: 42
<212> TYPE: DNA
<213> ORGANISM: Artificial Sequence
<220> FEATURE:
<223> OTHER INFORMATION: Synthetic DNA sequence that is a perfect
      complement to SEQ ID NO: 1

<400> SEQUENCE: 5
aataataaat aatatttaaa atttattata ggggattaag gg                      42

<210> SEQ ID NO 6
<211> LENGTH: 31
<212> TYPE: DNA
<213> ORGANISM: Artificial Sequence
<220> FEATURE:
<223> OTHER INFORMATION: Synthetic DNA strand having 1 guanine in the
      overhang after it hybridizes with SEQ ID NO: 1

<400> SEQUENCE: 6
attaataaat aatatttaaa atttattata g                                  31

<210> SEQ ID NO 7
<211> LENGTH: 33
<212> TYPE: DNA
<213> ORGANISM: Artificial Sequence
<220> FEATURE:
<223> OTHER INFORMATION: Synthetic DNA strand having 3 guanines in the
      overhang after it hybridizes with SEQ ID NO: 1

<400> SEQUENCE: 7
attaataaat aatatttaaa atttattata ggg                                33

<210> SEQ ID NO 8
<211> LENGTH: 36
<212> TYPE: DNA
<213> ORGANISM: Artificial Sequence
<220> FEATURE:
<223> OTHER INFORMATION: Synthetic DNA strand having 5 guanines in the
      overhang after it hybridizes with SEQ ID NO: 1

<400> SEQUENCE: 8
attaataaat aatatttaaa atttattata gggtgg                             36

<210> SEQ ID NO 9
<211> LENGTH: 38
<212> TYPE: DNA
<213> ORGANISM: Artificial Sequence
<220> FEATURE:
<223> OTHER INFORMATION: Synthetic DNA strand having 7 guanines in the
      overhang after it hybridizes with SEQ ID NO: 1

<400> SEQUENCE: 9
attaataaat aatatttaaa atttattata gggtgggg                           38

<210> SEQ ID NO 10
<211> LENGTH: 42
<212> TYPE: DNA
<213> ORGANISM: Artificial Sequence
```

```
<220> FEATURE:
<223> OTHER INFORMATION: Synthetic DNA strand having 10 guanines in the
      overhang after it hybridizes with SEQ ID NO: 1

<400> SEQUENCE: 10
attaataaat aatatttaaa atttattata gggtggggtg gg                            42

<210> SEQ ID NO 11
<211> LENGTH: 46
<212> TYPE: DNA
<213> ORGANISM: Artificial Sequence
<220> FEATURE:
<223> OTHER INFORMATION: Synthetic DNA strand having 13 guanines in the
      overhang after it hybridizes with SEQ ID NO: 1

<400> SEQUENCE: 11
attaataaat aatatttaaa atttattata gggtggggtg ggtggg                        46

<210> SEQ ID NO 12
<211> LENGTH: 48
<212> TYPE: DNA
<213> ORGANISM: Artificial Sequence
<220> FEATURE:
<223> OTHER INFORMATION: Synthetic DNA strand having 15 guanines in the
      overhang after it hybridizes with SEQ ID NO: 1

<400> SEQUENCE: 12
attaataaat aatatttaaa atttattata gggtggggtg gggtgggg                      48

<210> SEQ ID NO 13
<211> LENGTH: 42
<212> TYPE: DNA
<213> ORGANISM: Artificial Sequence
<220> FEATURE:
<223> OTHER INFORMATION: Synthetic Adenine-rich DNA strand, has 12
      adenines in the overhang after it hybridizes with SEQ ID NO: 1

<400> SEQUENCE: 13
attaataaat aatatttaaa atttattata aaaaaaaaaa aa                            42

<210> SEQ ID NO 14
<211> LENGTH: 42
<212> TYPE: DNA
<213> ORGANISM: Artificial Sequence
<220> FEATURE:
<223> OTHER INFORMATION: Synthetic thymine rich DNA strand, has 12
      thymines in the overhang after it hybridizes with SEQ ID NO: 1

<400> SEQUENCE: 14
attaataaat aatatttaaa atttattata tttttttttt tt                            42

<210> SEQ ID NO 15
<211> LENGTH: 42
<212> TYPE: DNA
<213> ORGANISM: Artificial Sequence
<220> FEATURE:
<223> OTHER INFORMATION: Synthetic cytosine-rich DNA strand, has 12
      cytosines in the overhang after it hybridizes with SEQ ID NO: 1

<400> SEQUENCE: 15
attaataaat aatatttaaa atttattata cccccccccc cc                            42

<210> SEQ ID NO 16
<211> LENGTH: 36
<212> TYPE: DNA
<213> ORGANISM: Artificial Sequence
<220> FEATURE:
<223> OTHER INFORMATION: Synthetic DNA strand that is the nanocluster-
```

-continued bearing portion of a NanoCluster Beacon probe embodiment

<400> SEQUENCE: 16
cccttaatcc cctgtagcta gaccaaaatc acctat                                36

<210> SEQ ID NO 17
<211> LENGTH: 39
<212> TYPE: DNA
<213> ORGANISM: Artificial Sequence
<220> FEATURE:
<223> OTHER INFORMATION: Synthetic DNA strand that is the guanine-rich
      portion of a NanoCluster Beacon probe embodiment

<400> SEQUENCE: 17
cccactccat cgagatttca cgggtggggt ggggtgggg                              39

<210> SEQ ID NO 18
<211> LENGTH: 80
<212> TYPE: DNA
<213> ORGANISM: Homo sapiens

<400> SEQUENCE: 18
agacctcaca gtaaaaatag gtgattttgg tctagctaca gtgaaatctc gatggagtgg       60
gtcccatcag tttgaacagt                                                  80

<210> SEQ ID NO 19
<211> LENGTH: 80
<212> TYPE: DNA
<213> ORGANISM: Homo sapiens

<400> SEQUENCE: 19
tgaaaatgac tgaatataaa cttgtggtag ttggagctgg tggcgtaggc aagagtgcct       60
tgacgataca gctaattcag                                                  80

<210> SEQ ID NO 20
<211> LENGTH: 18
<212> TYPE: DNA
<213> ORGANISM: Artificial Sequence
<220> FEATURE:
<223> OTHER INFORMATION: Synthetic DNA sequence that is the G-rich
      overhang of SEQ ID NO: 12 after hybridization

<400> SEQUENCE: 20
gggtggggtg gggtgggg                                                    18

<210> SEQ ID NO 21
<211> LENGTH: 42
<212> TYPE: DNA
<213> ORGANISM: Artificial Sequence
<220> FEATURE:
<223> OTHER INFORMATION: Synthetic nanocluster-bearing DNA strand

<400> SEQUENCE: 21
ccctttaacc cctataataa atttaaata ttatttatta at                          42

<210> SEQ ID NO 22
<211> LENGTH: 42
<212> TYPE: DNA
<213> ORGANISM: Artificial Sequence
<220> FEATURE:
<223> OTHER INFORMATION: Synthetic nanocluster-bearing DNA strand

<400> SEQUENCE: 22
cctccttcct cctataataa atttaaata ttatttatta at                          42

```
<210> SEQ ID NO 23
<211> LENGTH: 42
<212> TYPE: DNA
<213> ORGANISM: Artificial Sequence
<220> FEATURE:
<223> OTHER INFORMATION: Synthetic nanocluster-bearing DNA strand

<400> SEQUENCE: 23 ccccccccc cctataataa attttaaata ttatttatta at                42

<210> SEQ ID NO 24
<211> LENGTH: 42
<212> TYPE: DNA
<213> ORGANISM: Artificial Sequence
<220> FEATURE:
<223> OTHER INFORMATION: Synthetic nanocluster-bearing DNA strand

<400> SEQUENCE: 24
ccctataacc cctataataa attttaaata ttatttatta at                42

<210> SEQ ID NO 25
<211> LENGTH: 42
<212> TYPE: DNA
<213> ORGANISM: Artificial Sequence
<220> FEATURE:
<223> OTHER INFORMATION: Synthetic nanocluster-bearing DNA strand

<400> SEQUENCE: 25
ccctaactcc cctataataa attttaaata ttatttatta at                42

<210> SEQ ID NO 26
<211> LENGTH: 36
<212> TYPE: DNA
<213> ORGANISM: Artificial Sequence
<220> FEATURE:
<223> OTHER INFORMATION: Synthetic 36-base DNA strand, nanocluster
      bearing portion of probe for detecting Braf oncogene

<400> SEQUENCE: 26
cccttaatcc cctgtagcta gaccaaaatc acctat                       36

<210> SEQ ID NO 27
<211> LENGTH: 39
<212> TYPE: DNA
<213> ORGANISM: Artificial Sequence
<220> FEATURE:
<223> OTHER INFORMATION: Synthetic 39 base DNA strand, guanine-rich
      portion of probe for detecting Braf oncogene

<400> SEQUENCE: 27
cccactccat cgagatttca cgggtggggt ggggtgggg                    39

<210> SEQ ID NO 28
<211> LENGTH: 60
<212> TYPE: DNA
<213> ORGANISM: Influenza A virus

<400> SEQUENCE: 28
tttgggtctt attgctattt ccggcttgaa cttcttgctg tatcttgatg accccacaaa    60

<210> SEQ ID NO 29
<211> LENGTH: 40
<212> TYPE: DNA
<213> ORGANISM: Artificial Sequence
<220> FEATURE:
<223> OTHER INFORMATION: Synthetic 40 base DNA strand, nanocluster-
      bearing portion of probe for detecting Influenza A virus
```

-continued

```
<400> SEQUENCE: 29
cccttaatcc cctatttcaa gcgggaaata gcaataagac                              40

<210> SEQ ID NO 30
<211> LENGTH: 45
<212> TYPE: DNA
<213> ORGANISM: Artificial Sequence
<220> FEATURE:
<223> OTHER INFORMATION: Synthetic 45 base DNA strand, guanine-rich
      portion of probe for detecting Influenza A virus

<400> SEQUENCE: 30
gggtcatcaa gatacagcaa gaagataggg tggggtgggg tgggg                       45

<210> SEQ ID NO 31
<211> LENGTH: 12
<212> TYPE: DNA
<213> ORGANISM: Artificial Sequence
<220> FEATURE:
<223> OTHER INFORMATION: Synthetic DNA sequence
<220> FEATURE:
<221> NAME/KEY: misc_feature
<222> LOCATION: (4)..(8)
<223> OTHER INFORMATION: n may be adenine or thymine

<400> SEQUENCE: 31
cccnnnnncc cc                                                           12
```